(12) United States Patent
Jang

(10) Patent No.: US 6,783,543 B2
(45) Date of Patent: Aug. 31, 2004

(54) INTRAVASCULAR STENT WITH INCREASING COATING RETAINING CAPACITY

(75) Inventor: G. David Jang, Redlands, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/874,349

(22) Filed: Jun. 4, 2001

(65) Prior Publication Data

US 2004/0148012 A9 Jul. 29, 2004

Related U.S. Application Data

(60) Provisional application No. 60/235,164, filed on Sep. 23, 2000, and provisional application No. 60/209,255, filed on Jun. 5, 2000.

(51) Int. Cl.[7] ................................................. A61F 2/06
(52) U.S. Cl. ...................................... 623/1.15; 623/1.45
(58) Field of Search ............................. 623/1.1, 1.11, 623/1.12–1.22, 1.39, 1.42, 1.44–1.48

(56) References Cited

U.S. PATENT DOCUMENTS

| | | | |
|---|---|---|---|
| 5,523,092 A | 6/1996 | Hanson et al. ............ 424/423 |
| 5,810,767 A | 9/1998 | Klein ........................ 604/53 |
| 5,843,172 A | 12/1998 | Yan ............................. 623/1 |
| 5,876,449 A | 3/1999 | Starck et al. ................. 623/12 |
| 5,922,020 A | 7/1999 | Klein et al. .................. 623/1 |
| 5,972,027 A | 10/1999 | Johnson ..................... 623/1 |
| 6,042,606 A | 3/2000 | Frantzen ..................... 623/1 |
| 6,162,243 A | 12/2000 | Gray et al. .................. 623/1.11 |
| 6,190,404 B1 | 2/2001 | Palmaz et al. .............. 623/1.15 |
| 6,206,915 B1 | 3/2001 | Fagan et al. ............... 623/1.42 |
| 6,206,916 B1 | 3/2001 | Furst ........................ 623/1.46 |
| 6,231,598 B1 | 5/2001 | Berry et al. ............... 623/1.15 |
| 6,241,762 B1 | 6/2001 | Shanley ..................... 623/1.17 |
| 6,254,632 B1 | 7/2001 | Wu et al. ................... 623/1.15 |
| 6,258,121 B1 | 7/2001 | Yang et al. ................. 623/1.46 |
| 6,261,320 B1 * | 7/2001 | Tam et al. .................. 623/1.15 |
| 6,273,908 B1 | 8/2001 | Ndondo-Lay ............... 623/1 |
| 6,273,913 B1 | 8/2001 | Wright et al. .............. 623/1.42 |
| 6,280,413 B1 | 8/2001 | Clark et al. ................ 604/104 |
| 6,379,381 B1 * | 4/2002 | Hossainy et al. .......... 623/1.42 |
| 6,506,437 B1 | 1/2003 | Harish et al. .............. 427/2.25 |
| 6,558,422 B1 | 5/2003 | Baker et al. ............... 623/16.11 |
| 6,562,065 B1 | 5/2003 | Shanley ..................... 623/1.15 |

FOREIGN PATENT DOCUMENTS

| | | | |
|---|---|---|---|
| EP | 0 950 386 A2 | 10/1999 | ............ A61F/2/06 |
| WO | 9626689 | 9/1996 | |
| WO | WO 98/23228 | 6/1998 | ............ A61F/2/06 |
| WO | WO 98/36784 | 8/1998 | ........... A61L/29/00 |
| WO | 99/01088 | 1/1999 | |
| WO | 99/15108 | 4/1999 | |
| WO | WO 99/23977 | 5/1999 | ............ A61F/2/06 |
| WO | 01/26584 | 4/2001 | |
| WO | 01/66036 | 9/2001 | |
| WO | 01/91918 | 12/2001 | |
| WO | 01/93781 | 12/2001 | |

* cited by examiner

Primary Examiner—Corrine McDermott
Assistant Examiner—Hieu Phan
(74) Attorney, Agent, or Firm—Jones Day

(57) ABSTRACT

An expandable stent includes a tubular structure with an outer surface positionable adjacent to a vessel wall and an inner surface facing a lumen of a body passageway. The tubular structure further includes a plurality of expansion struts, connector struts and cells. The tubular structure has a first diameter which permits intraluminal delivery of the tubular structure into the body passageway, and a second expanded and deformed diameter which is achieved upon the application of a radially, outwardly extending force. A plurality of cavities are formed in the outer surface of the stent.

21 Claims, 7 Drawing Sheets

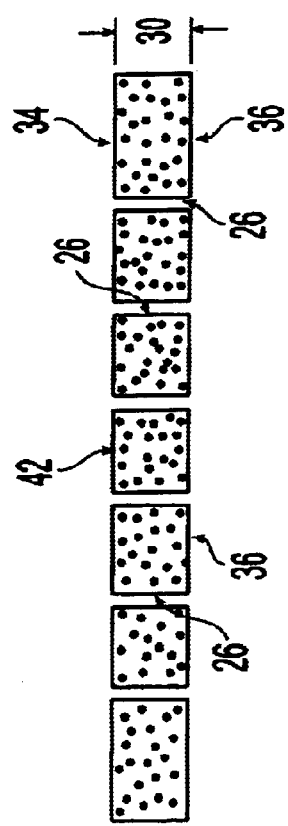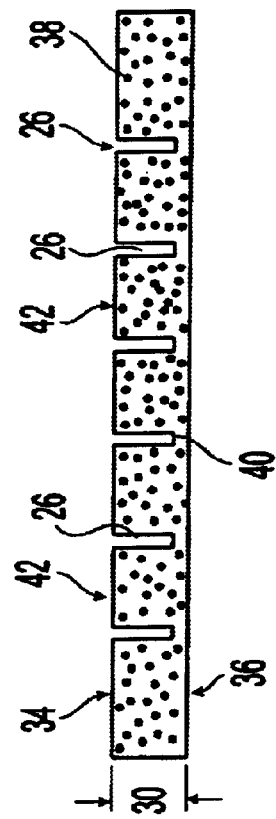

INTRAVASCULAR STENT WITH INCREASING COATING RETAINING CAPACITY

CROSS-REFERENCE TO RELATED APPLICATIONS

This application claims the benefit of Provisional Patent Application No. 60/209,255 filed Jun. 5, 2000, the disclosure of which is incorporated by reference.

BACKGROUND OF THE INVENTION

1. Field of Invention

This invention relates generally to intravascular stents, and more particularly to intravascular stents that include a plurality of cavities formed on a surface of the stent and are coated with a restenosis inhibiting agent.

2. Description of the Related Art

By 1999, the percutaneous balloon angioplasty and stent implant procedures have become the dominant non-surgical revascularization method of the atherosclerotic stenosis, or obstruction, of the vascular lumen, and particularly in the coronary vascular system in the heart. With balloon angioplasty alone, without use of stent, the restenosis rate after angioplasty has been as high as 25–45% in the first time clinical cases. With use of stents after balloon angioplasty, the restenosis has been reduced significantly. Even so, the restenosis rate after stent implant is reported as 10–25% range depending on the condition of the vessel stented or what specific stent was used, requiring a need for further restenosis reducing measures after intravascular stenting.

To further reduce the restenosis rate after stent implant, numerous means has been tried, including laser, atherectomy, high frequency ultrasound, radiation device, local drug delivery, etc. Although the brachytherapy (radiation treatment) has proved to be reasonably effective in further reducing restenosis after stent implant, using brachytherpy is very cumbersome, inconvenient and costly. Mainly because it is radioactive device and radiation therapy specialist from another department has to be involved with the interventional cardiologist in the cardiac catheterization laboratory. The laser and atherectomy devices proved to be marginally useful in this purpose with added costs.

The local drug therapy appears be a very promising method for the future, as better pharmaceutical, chemical or biogenetic agents are developed and became available. Some research data, both from animal tests and human clinical studies, indicate that there are evidences of suppressing restenosis after stent implant when certain growth blocking pharmaceutical agents available today are used to coat the stent. In another instances, it has been speculated that certain surface modifying materials coated on the surface of the stent may be beneficial by it alone or in combination with growth suppressing agent, in reducing restenosis rate. In either instance, the drug or substance should be locally attached or coated on the stent and in sufficient amounts. However, attaching or coating a sufficient amount of a substance or drug on the coronary stent is not so easy a proposition.

Coating a drug or an agent on the surface of the stent has a demanding problem of enough volume of such substance coated on the small surface areas of stent struts, without increasing the physical width or thickness of stent struts. This demand directly conflicts with the metal fraction issue of the stent. If the width (and lesser degree the thickness) of stent struts is increased in order to widen drug coating surface areas, it would have an elevated deleterious foreign body effect of the increased metal fraction of the stent, which would promote restenosis.

Designing an ideal stent, particularly the coronary stent, is a very demanding balance of a numerous conflicting factors. An ideal stent requires an ideal balance of numerous different stent features built into the stent. One of the many requirements of a coronary, or any vascular stent, is to keep the metal fraction of the stent low. This means that drug coating is a very demanding task. Enough amounts of a drug or agent should be coated on the miniscule surface areas of the stent struts, in order to have the desired drug results of reducing restenosis. An average stent, particularly a coronary stent, will have problem of providing desired amount of drug-retaining capacity on the surface areas of the stent struts.

The main invention of this application is not an invention of the stent itself. The present invention is the particular measures designed to increase drug coating or attachment capacity of a stent by adding exposed surface areas or reservoir capacity of the stent, without increasing the width or thickness of the stent struts or without increasing the metal fraction of the stent. These special measures of present invention will enhance the coating substances to a stent. Further, the present invention will enhance the reservoir capacity of the stent for different forms of restenosis reducing proteins, chemicals or drugs, and will prolong the releasing time duration of the substances.

U.S. Pat. No. 6,190,404 discloses an intravascular stent with an outer surface, an inner surface and grooves formed in the inner surface of the stent. The grooves are positioned and provided to increase the rate of migration of endothelial cells upon the inner surface of the stent.

There is a need for a stent with a geometry that provides for an increased amount of a coating substance. There is a further need for a stent that includes reservoirs for retaining coatings.

SUMMARY OF THE INVENTION

Accordingly, an object of the present invention is to provide an intravascular stent with a geometry that provides for an increased amount of a coating substance. Another object of the present invention is to provide an intravascular stent with cavities formed in the stent that serve as reservoirs of coatings applied to the stent. Yet another object of the present invention is to provide an intravascular stent with cavities formed in the body of the stent and with a restenosis inhibiting agent applied to the stent.

Another object of the present invention is to provide an intravascular stent with micro-holes or micro-slits that provide reservoirs for stent coatings. These and other objects of the present invention are achieved in an expandable stent. A tubular structure includes an outer surface positionable adjacent to a vessel wall and an inner surface facing a lumen of a body passageway. The tubular structure further includes a plurality of expansion struts, connector struts and cells. The tubular structure has a first diameter which permits intraluminal delivery of the tubular structure into the body passageway, and a second expanded and deformed diameter which is achieved upon the application of a radially, outwardly extending force. A plurality of cavities are formed in the outer surface of the stent.

In another embodiment of the present invention, an expandable stent, includes a tubular structure with an outer surface positionable adjacent to a vessel wall, an inner surface facing a lumen of a body passageway, a plurality of expansion struts, connector struts and cells. The tubular structure has a first diameter which permits intraluminal delivery of the tubular structure into the body passageway, and a second expanded and deformed diameter that is achieved upon the application of a radially, outwardly extending force. A plurality of cavities formed in the outer surface of the stent. A coating substance is on at least a portion of outer surface of the stent including and extends into at least a portion of the cavities.

In another embodiment of the present invention, a stent assembly includes a balloon and an expandable stent positioned at an exterior of the balloon. The stent includes a tubular structure with an outer surface positionable adjacent to a vessel wall, an inner surface facing a lumen of a body passageway, a plurality of expansion struts, connector struts and cells. The tubular structure has a first diameter which permits intraluminal delivery of the tubular structure into the body passageway, and a second expanded and deformed diameter that is achieved upon the application of a radially, outwardly extending force applied by the balloon. A plurality of cavities are formed in the outer surface of the stent. A coating substance is on at least a portion of outer surface of the stent including and extending into at least a portion of the cavities.

In another embodiment of the present invention, a method of manufacturing an intravascular stent is provided. The intravascular stent has an inner surface and an outer surface. A plurality of cavities are formed on the outer surface. A coating substance that inhibits restenosis is formed on at least a portion of the outer surface and on at least a portion of the plurality of cavities

BRIEF DESCRIPTION OF DRAWINGS

FIG. 3a is a cross-section, side view of a stent of the present invention with cavities that extend from the outer surface through the inner surface.

FIG. 3(b) is a cross-sectional, magnified, side view of one embodiment of the stent of the present invention illustrating that cavities can be closed and serve as reservoirs for coating substance applied to the stent.

DETAILED DESCRIPTION OF THE PREFERRED EMBODIMENTS

Figure 1:
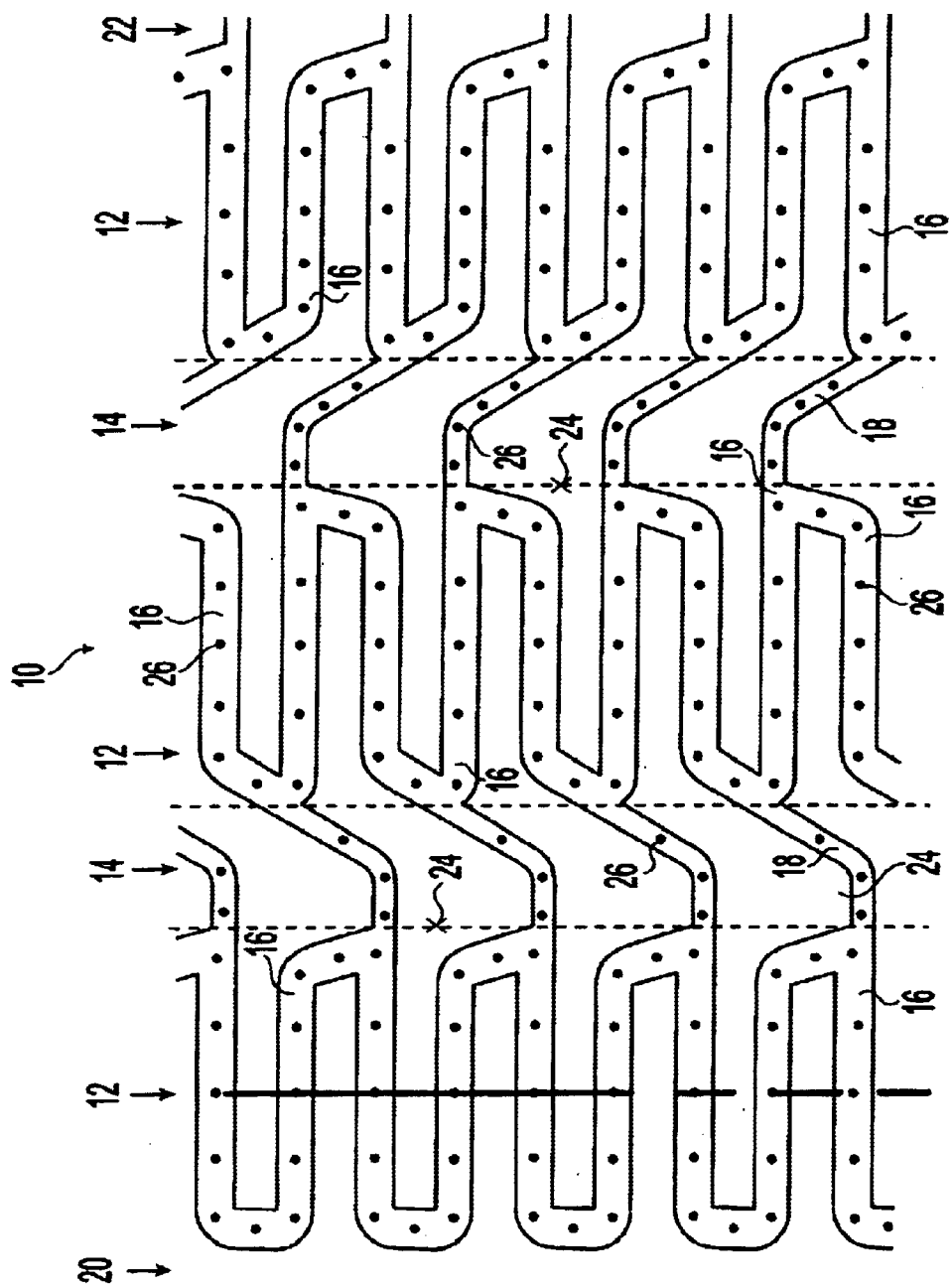
FIG. 1 is a flat cut-open, two-dimensional, schematic view of one embodiment of a stent of the present invention that includes cavities formed in the body of the stent.

Referring now to FIG. 1, one embodiment of an expandable stent 10 of the present invention is illustrated. A tubular structure includes an outer surface positionable adjacent to a vessel wall and an inner surface facing a lumen of a body passageway. The tubular structure further includes a plurality of expansion struts, connector struts and cells. The tubular structure has a first diameter which permits intraluminal delivery of the tubular structure into the body passageway, and a second expanded and deformed diameter which is achieved upon the application of a radially, outwardly extending force.

A plurality of cavities are formed in the outer surface of the stent. The cavities can be micro-holes or micro-slits and extend from the outer surface to an interior of the struts, or extend from the outer surface all the way through the inner surface. An example of a stent design useful with the present invention is disclosed in U.S. Pat. No. 5,954,743, incorporated herein by reference. In FIG. 1, a two-dimensional view of the stent 10 is illustrated and is seen from the outer surface of the cut-open, two-dimensional view.

Stent 10 includes expansion columns 12 and connector columns 14 in a continuous and alternating pattern to form a longitudinal dimension and a vertical dimension. The vertical and longitudinal dimensions determine the circumference and the length respectively of stent 10. Expansion columns 12 have expansion struts 16 in a vertical zigzag or corrugated pattern. One expansion column 12 is linked to an adjacent expansion column 12 by connector column 14 between two adjacent expansion 12 columns. Connector columns 14 have connector struts 18 that serve as linking arms between expansion struts 16 in two adjacent expansion columns 12. Stent 10 has a proximal end 20 and a truncated end 22 in the middle of stent 10.

In one embodiment, stent 10 is a tubular structure that includes patterned expansion struts 16 and connectors struts 18 continuously linked circumferentially and longitudinally with a predetermined length. The total surface areas of struts 16 and 18 are limited to a certain percent of the total cylindrical surface area of tubular stent 10, particularly when stent 10 is expanded in a vessel, with enlarged (by stent expansion) stent cells 24 that make up the remainder of the total stent surface area.

The amount of a coating substance applied to and retained by stent 10 is determined by the total surface area of stent struts 16 and 18. Coating substance is preferably a restenosis inhibiting agent that is a drug, polymer and bio-engineered material and combinations thereof. It will be appreciated that other types of coating substances, well known to those skilled in the art, can be applied to stent 10 of the present invention. Because the total stent strut surface areas are limited in size, the amount of coating substance applied to stent 10 is limited to a small volume. When stent 10 is expanded in a vessel the relative surface area of struts 16 and 18 decreases in relation to the areas of stent cells 24. The total cylindrical surface area of stent 10 when it is implanted and expanded inside of a vessel is equal to the sum of the strut surface areas, which do not change, and stent cells 24 areas. The size of stent cells 24 areas changes when stent 10 is expanded. The present invention increases the amount of the coating substance capacity of stent 10 without increase the metal fraction of stent 10.

In various embodiments, the present invention increases the coating substance retaining capacity of stent 10 by forming cavities that can be micro holes 26 which are made, punched, drilled or burned into the expansion and connector struts 16. In FIG. 1, micro holes 26 have openings 28 on outer surface of struts 16 and 18. Micro holes 26 are made and arranged in such a way so that they can be evenly distributed in struts 16 and 18. In this embodiment, micro holes 26 are evenly distributed through out the entire body of stent 10. The number of micro holes 26 illustrated in FIG. 1 is only by example.

Figure 2:
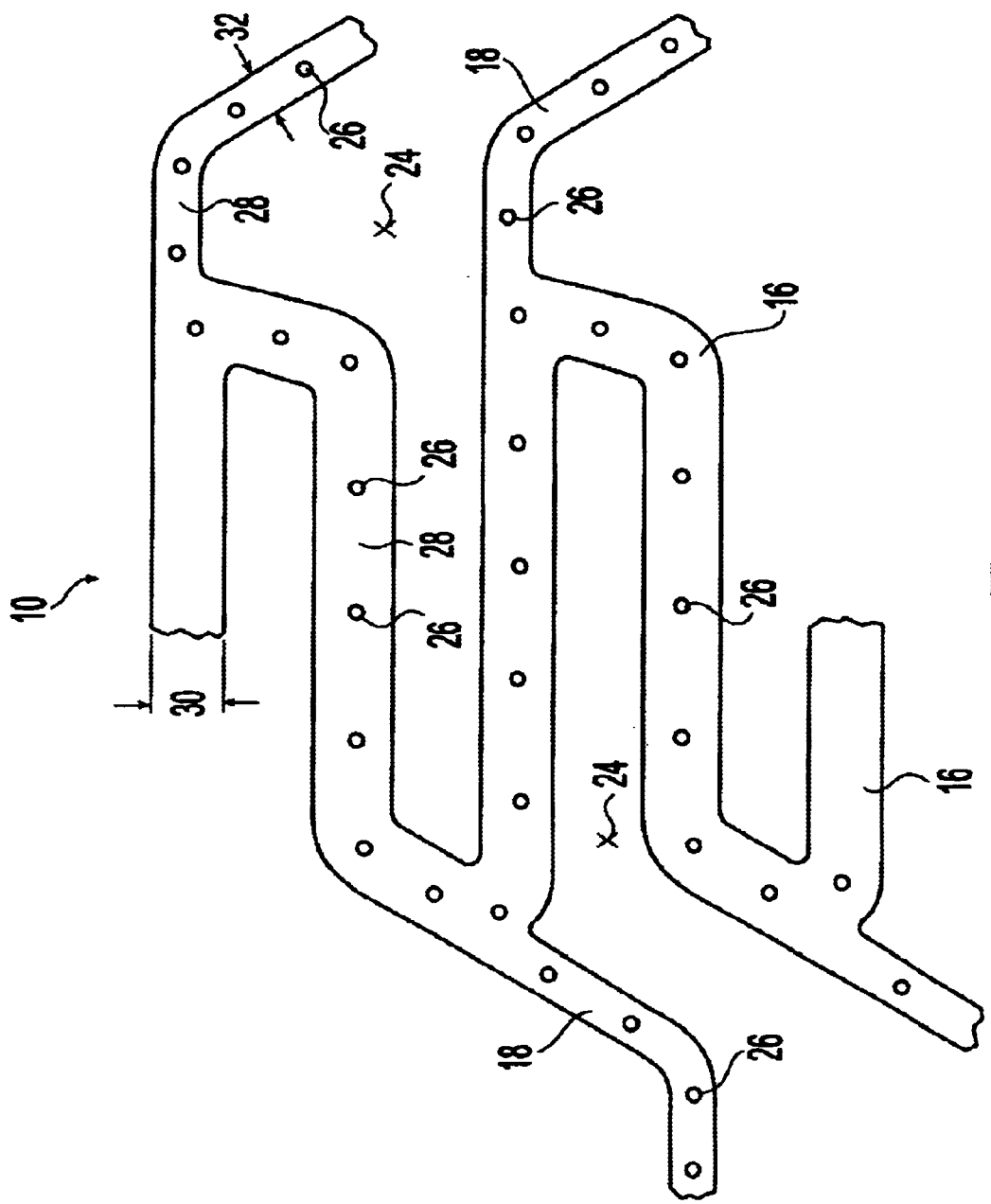
FIG. 2 is a close-up view of the stent from FIG. 1 with cavities that extend from the outer surface of the stent into an interior of the stent.

The number of micro holes 26 created in stent 10 can vary by increasing or decreasing the number according to the necessity and requirements when such stents are fabricated for clinical use. Additionally, the pattern of creating micro holes 26 in stent struts 16 and 18 can be varied according to the clinical and protocol needs. Although micro holes 26 in FIG. 1 are made in straight lines it will be appreciated that micro holes 26 can be made in any varied pattern or shape. Micro-holes 26 can be made to form any suitable shape or pattern as necessary, if they meet the structural or engineering requirements of stent 10. Micro holes 26 can be made in single line or in multiple lines in struts 16 and 18 and arranged in any pattern. In the embodiment illustrated in FIG. 2, width 30 of expansion strut 16 is shown as being larger than width 32 of connector strut 18. It will be appreciated that the relative widths can change and that width 32 can be greater than width 30.

The size of micro holes 26 can be based on the physical dimensions of struts 16 and 18. Micro holes 26 cannot have diameters or size as large as the width of struts 16 and 18. Micro holes 26 can have substantially smaller widths or diameters than widths 30 and 32 in order to maintain the structural integrity and radial strength of stent 10. In one embodiment, micro holes 26 have an effective size or diameter to provide an optimal retaining capacity of substances or drugs that are coated or deposited on stent 10. Similarly, the distance between micro holes 26 is selected to maintain the integrity of stent 10 while providing an optimal number of micro holes 26 to provide a sufficient coating substance retaining capacity. Micro holes 26 in struts 18 can be made smaller than micro holes 26 in expansion struts 16 and visa versa.

Micro holes 26 and opening 28 can have more than one shape including but not limited to circular, square, oval, oblong, irregular, polygonal or a combination thereof, depending on the method used to create micro holes 26. The tools to create micro holes 26 can be mechanical, photochemical, laser, EDM and the like. The shape or configuration of micro holes 26 and openings 28 in stent struts 16 and 18 can be influenced by the size or diameter of the micro hole 26 made, as well as by other manufacturing factors such as a laser beam size, photochemical resolution or EDM cathode and the like.

In the embodiment of FIG. 3(a), micro holes 26 penetrate the entire widths 30 and 32 of struts 16 and 18 at a perpendicular angle with opening 28 on both outer surface 34 and inner surface 36. Shaded areas 38 show the cross-sectional cut surface of struts 16 and 18. Micro holes 26 are created in a regular interval with the uninterrupted segment 28 between micro holes 26. Micro holes 26 communicate freely between outer surface 34 and inner surface 36. As can be seen, micro holes 26 increase the contact surface areas of stent struts 16 or 18 for the purpose of increasing the capacity of retaining the intended coating substance added to stent 10. The bore space of micro holes 26 also serve as micro reservoir chambers for the substance to be added, attached or coated to stent 10. When stent 10 is electropolished, the shape or dimension of micro holes 26 can be slightly changed.

FIG. 3(b) illustrates an embodiment where micro holes 36 are blind and extend from outer surface 34 but not do not continue to inner surface 36. Shaded areas 38 indicate cross-sectioned stent struts 16 and 18. In FIG. 3(b), micro holes 26 have cul de sac geometry's 40 that terminate in an interior of struts 16 and 18. Cul-de-sacs 40 serve as reservoirs for coating substances applied to stent 10. Cul-de-sacs 40 can be created at regular or irregular intervals with uninterrupted segments 42 between that are formed between micro holes 26.

Figure 3C:
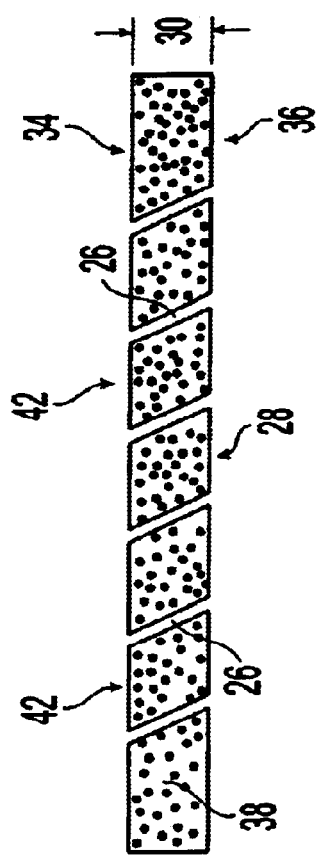
FIG. 3(c) is a cross-sectional, magnified view of another embodiment of the present invention illustrating a stent that includes cavities that extent at a slant angle from the outer surface through the inner surface.

Referring now to FIG. 3(c), micro holes 26 are shown with their axes at a slant angle relative to stent struts 16 and 18. In this embodiment, micro holes 26 extend from outer surface 34 to inner surface 36. Because micro holes 26 have a slant angle through in this embodiment, the length and reservoir capacity of the micro holes 26 is increased compared to the capacity of the FIG. 3(a) micro holes 26.

Figure 3D:
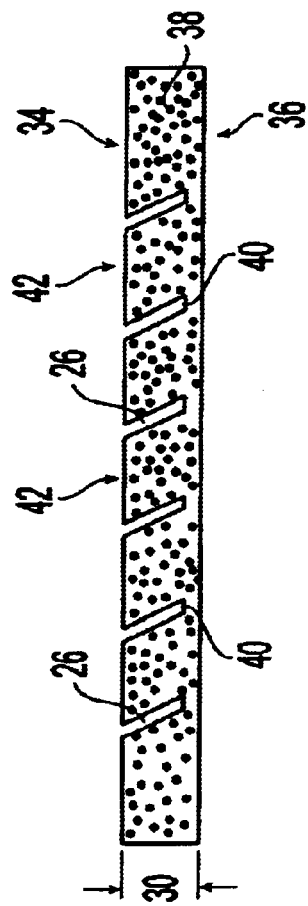
FIG. 3(d) is a cross-sectional, magnified, side view of one embodiment of the present invention with cavities that extend at a slant, non-perpendicular angle from the outer surface to an interior of the stent.

In the embodiment illustrated in FIG. 3(d), micro holes 26 have openings 28 on outer surface 34 and cul de sacs 40 on inner surface 36, all formed at a slant angle. Outer surface 34 has uninterrupted segments 42 between slant angled micro holes 26 and inner surface 36 is smooth without openings 28. Again, cul-de-sac 40 provides a reservoir for a coating substance applied to stent 10. Because the bore space of micro holes is at a slant angle there is an increased reservoir capacity.

Figure 4:
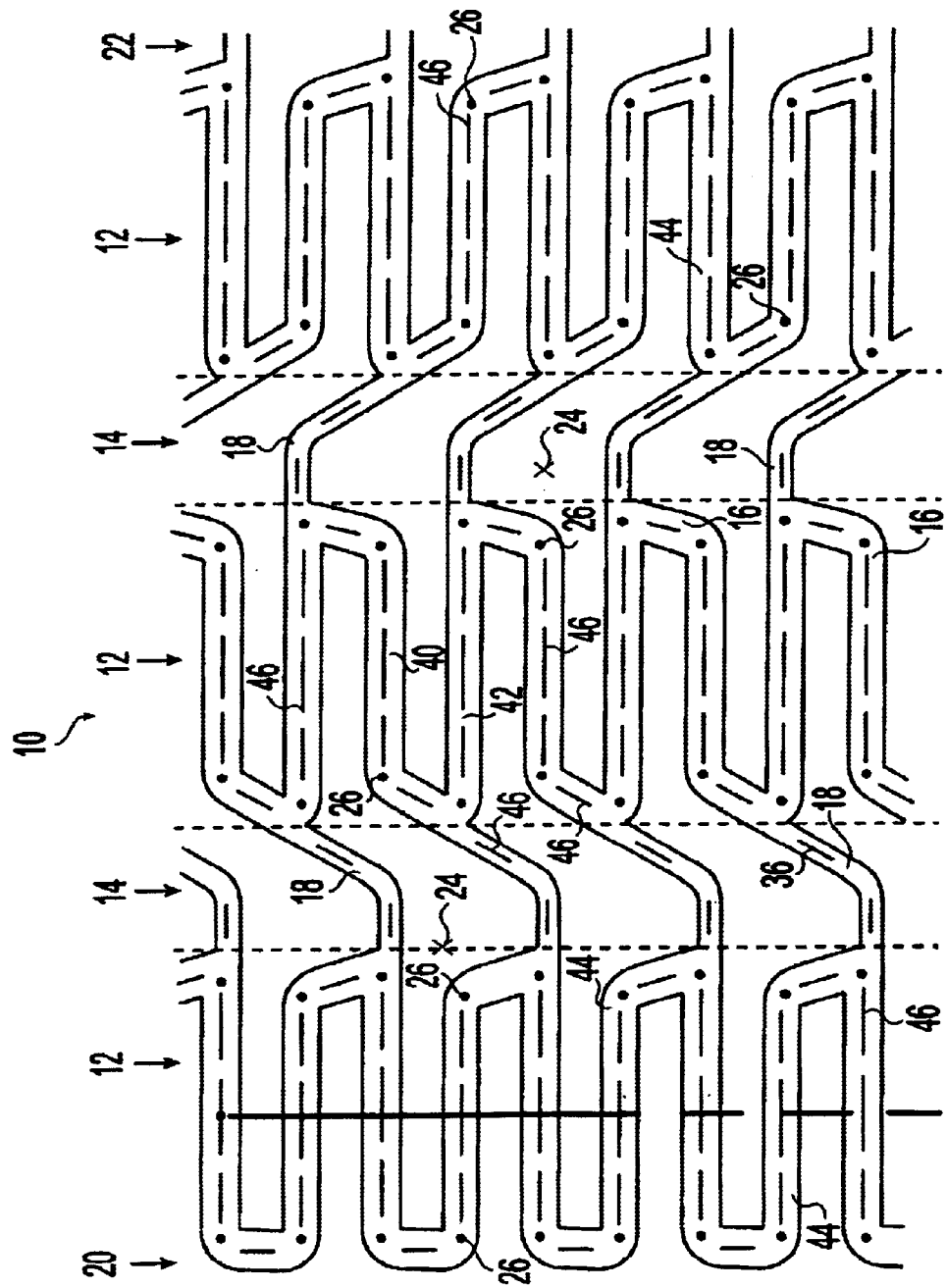
FIG. 4 is a flat cut-open, two-dimensional, schematic view of a stent seen from the outer surface of the stent cavities distributed in an even pattern

In contrast to FIG. 1, the cavities formed in FIG. 4 are micro slits, groves, and the like, collectively denoted as 40, which have widths 44 that are larger than openings 36. Compared to micro holes 26 of FIG. 1, the micro slits 40 shown in FIG. 4 provide a larger reservoir capacity for the coating substance.

Micro slits 40 can be evenly or unevenly distributed in struts 16 and 18. The number of micro slits 40 illustrated in FIG. 4 is only by way of example. Increasing or decreasing the number of micro slits 40 created in stent 10 may vary according to the clinical and pharmcodynamic necessity and requirements. Additionally, the pattern of creating micro slits 40 in struts 16 and 18 can vary according to the clinical and engineering needs. Although micro slits 40 illustrated in FIG. 4 are in straight lines, micro slits 40 can be made in curvilinear, square-angles, slant angled and the like with or without radius of curvature. Micro slits 40 can be made in any suitable pattern or shape as required, if they meet the structural or engineering requirements of stent 10. Micro slits 40 can be made in single line or in multiple lines in struts 16 and 18 and arranged in any other pattern. The FIG. 4 embodiment illustrates that micro holes 26 can also be included in the same stent 10.

Figure 5:
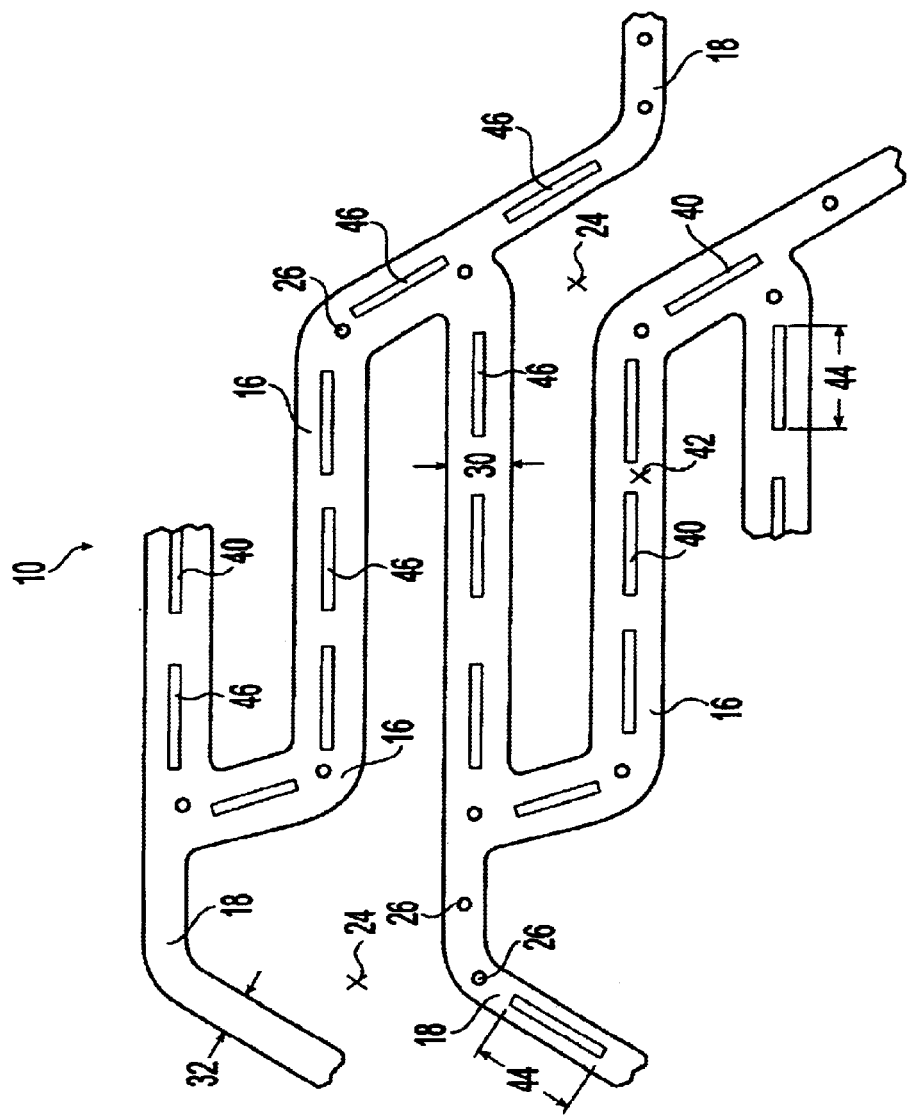
FIG. 5 is a close-up, magnified, view of the expansion and connector struts from FIG. 4 with micro-slits and micro-holes that extend from the outer surface of the stent struts.

The magnified view of stent 10 illustrated in FIG. 5 shows struts 16 and 18 with micro slits 40 and openings 46 on outer surface 34 of stent 10. Width 34 of expansion strut 16 is larger than width 32 of strut 18 in this embodiment. However, widths 34 and 32 can be the same in size or even reversed.

Width 44 of micro slit 40 is determined by the physical dimensions and limits of struts 16 and 18. Width 44 can not be made as large as widths 34 and 32. Width 44 is substantially smaller than width 34 in order to maintain the structural integrity and radial strength of stent 10. The length of micro slit 40 can be made as long as stent struts 16 and 18. The length of micro slit 40 can be shorter or longer than the width of struts 16 and 18. Similarly, the uninterrupted distance 42 between micro slits 40 is selected so that the structural integrity of stent 10 is not compromised. Within the allowable limits, micro slits 40 can be made in different sizes or dimensions in same or differing patterns. Micro slits 40 in struts 18 can be made smaller than, the same as or greater than micro-slits 40 formed in struts 16.

The shape of micro slits 40 and opening 46 can be different than that illustrated in FIG. 5. The geometry of micro slits 40 can be straight linear, curvilinear, angled, squared or any other shape, depending on the design of stent 10 and the method used to make micro slits 40 during the manufacturing process. The tools to create the micro slits 40 can be the same as those used for micro-holes 26. Different shapes, sizes and positions of micro slits 40 can be included in an individual stent 10.

Figure 6A:
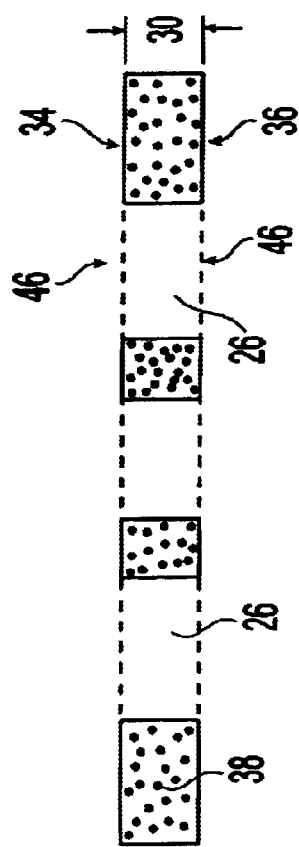
FIG. 6(a) is a cross-sectional, magnified, side view of a stent strut of the present invention illustrating micro slits that extend through both the outer and inner surfaces and the entire thickness of the stent strut.

Referring now to FIG. 6(a), micro slits 40 can extend through struts 16 and 18 with openings 50 on both outer and inner surfaces 34 and 36. Micro slits 40 can be created in a regular interval with uninterrupted segment 42 between micro slits 40.

Additionally, in this embodiment micro slits 40 can communicate freely between outer surface 34 inner surface 36. Micro slits 40 increase coating substance contact surface areas of struts 16 and 18 for the purpose of increasing the reservoir capacity of intended coating substances.

Figure 6B:
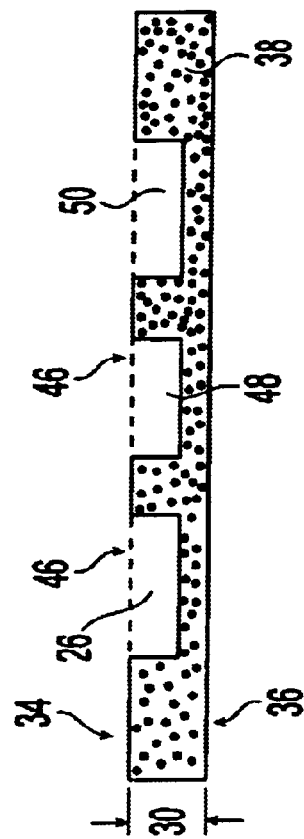
FIG. 6(b) is a cross-sectional, magnified, side view of the stent strut of the present invention illustrating perpendicularly extending open micro slits on one side and closed micro-slits on the opposite site of the strut.

FIG. 6(b) illustrates that blind micro slits 40 partially extend into struts 16 and 18 from outer surface 34. Blind micro slits 40 end in cul-de-sacs 48 which can be of any desired geometric configuration. Cul-de-sacs 48 create micro reservoirs 50 for coating substances and can be formed at regular or irregular intervals with uninterrupted segments 42 between blind micro slits 48. Generally, the reservoir capacity of blind micro slits 40 is greater than that of blind micro holes 26. Additionally, Micro slits 40 can also be made in slant angles.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An expandable stent, comprising:
    a tubular structure including an outer surface positionable adjacent to a vessel wall, an inner surface facing a lumen of a body passageway, a plurality of expansion struts that are substantially parallel to each other, connector struts, and cells, the tubular structure having a first diameter that permits intraluminal delivery of the tubular structure into the body passageway, and a second expanded and deformed diameter upon the application from the interior of the tubular member of a radially, outwardly extending force; and
    a plurality of cavities formed in the outer surface of the stent wherein the plurality of cavities are micro-holes or micro-slits that extend from the outer surface through the inner surface, and wherein the micro-holes or micro-slits are configured to provide a plurality of reservoirs for a substance; and
    a substance contained in said reservoirs.

2. The stent of claim 1, wherein the tubular structure is balloon expandable.

3. The stent of claim 1, wherein the tubular structure is self-expandable.

4. The stent of claim 1, wherein at least a portion of the tubular structure is made of a shape memory alloy.

5. The stent of claim 1, wherein the plurality of cavities are substantially evenly positioned on the tubular structure.

6. The stent of claim 1, wherein the plurality of cavities increases the flexibility of the stent without substantially reducing the radial strength of the stent in a deployed state.

7. The stent of claim 1, wherein the micro-holes or micro-slits have a cross-section that is smaller than a cross-section of a strut.

8. The stent of claim 1, further comprising a plurality of micro-holes or micro-slits that extend from the outer surface to an interior of the tubular structure without extending through the inner surface.

9. The stent of claim 1, wherein at least a portion of the micro-holes have a diameter of at least 0.0007 inch.

10. The stent of claim 1, wherein at least a portion of the micro-holes or micro-slits extend perpendicular from the outer surface to an interior of the tubular structure.

11. An expandable stent, comprising:
    a tubular structure including an outer surface positionable adjacent to a vessel wall, an inner surface facing a lumen of a body passageway, a plurality of expansion struts that are substantially parallel to each other, connector struts, and cells, the tubular structure having a first diameter that permits intraluminal delivery of the tubular structure into the body passageway, and a second expanded and deformed diameter upon the application from the interior of the tubular member of a radially, outwardly extending force;
    a plurality of cavities formed in the outer surface of the stent wherein the plurality of cavities are micro-holes or micro-slits that extend from the outer surface through the inner surface, and wherein the micro-holes or micro-slits are configured to provide a plurality of reservoirs for a substance; and
    a substance disposed on at least a portion of outer surface of the stent including and extending into at least a portion of the cavities contained in said reservoirs.

12. The stent of claim 11, further comprising the substance disposed on at least a portion of the inner surface of the stent.

13. The stent of claim 11, wherein the substance is a restenosis inhibiting agent.

14. The stent of claim 13, wherein the restenosis inhibiting agent is selected from a drug, polymer and bio-engineered material.

15. The stent of claim 13, wherein the restenosis inhibiting agent is a combination of two agents selected from a drug, polymer and bio-engineered material.

16. The stent of claim 11, wherein the tubular structure is balloon expandable.

17. The stent of claim 11, wherein the tubular structure is self-expandable.

18. The stent of claim 11, wherein at least a portion of the tubular structure is made of a shape memory alloy.

19. The stent of claim 11, wherein the plurality of cavities are substantially evenly positioned on the tubular structure.

20. The stent of claim 11, wherein the plurality of cavities increases the flexibility of the stent without substantially reducing the radial strength of the stent in a deployed state.

21. The stent of claim 11, wherein the micro-holes or micro-slits have a cross-section that is smaller than a cross-section of a strut.

* * * * *